US00PP36372P2

(12) United States Plant Patent
Koot

(10) Patent No.: US PP36,372 P2
(45) Date of Patent: Jan. 7, 2025

(54) ***VERBENA* PLANT NAMED 'Doveremsunwhi 24'**

(50) Latin Name: ***Verbena* X *hybrida***
Varietal Denomination: Doveremsunwhi 24

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/388,189

(22) Filed: Nov. 8, 2023

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
CPC ..... A01H 5/02; A01H 5/00; A01H 6/86
See application file for complete search history.

(56) References Cited

PUBLICATIONS

Dummen Orange Empress Sun White 2024, retrieved on Mar. 11, 2024 at https://na.dummenorange.com/app/es/products/usa/verbena/empress-sun-white-2024/PAT_42557, 4 pp. (Year: 2024).*
Welby Gardens Hardy Starts 2024 Program, The Plant Connection, retrieved on Mar. 11, 2024 at https://www.bfgsupply.com/media/7913/2024-welby-product-program.pdf, 4 pp. (Year: 2024).*

* cited by examiner

*Primary Examiner* — June Hwu
(74) *Attorney, Agent, or Firm* — C. Anne Whealy

(57) ABSTRACT

A new and distinct cultivar of *Verbena* plant named 'Doveremsunwhi 24', characterized by its relatively compact, mounding to semi-trailing plant habit; moderately vigorous growth habit and moderate growth rate; freely branching habit; early and freely flowering habit; large white-colored flowers; and good container and garden performance.

2 Drawing Sheets

Figure 1:
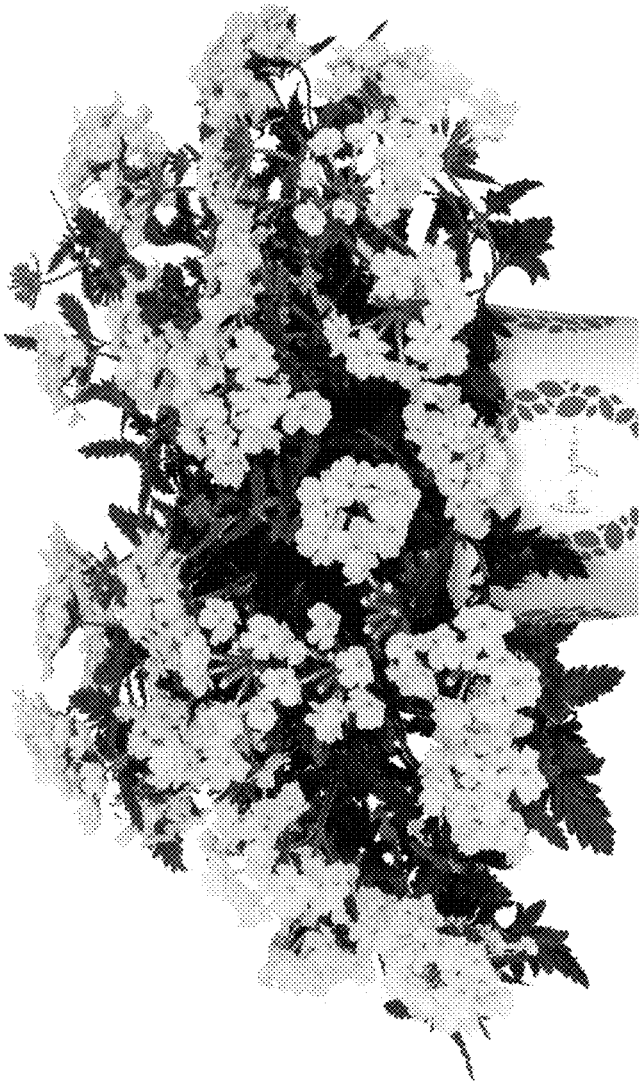

Botanical designation: *Verbena* X *hybrida*.
Cultivar denomination: 'DOVEREMSUNWHI 24'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Verbena* plant, botanically known as *Verbena* X *hybrida* and hereinafter referred to by the name 'Doveremsunwhi 24'.

The new *Verbena* plant is a product of a planned breeding program conducted by the Inventor in Rheinberg, Germany. The objective of the breeding program is to create new freely branching and early flowering *Verbena* plants with numerous large attractive flowers.

The new *Verbena* plant originated from a cross-pollination made by the Inventor in July 2020 in Rheinberg, Germany of a proprietary selection of *Verbena* X *hybrida* identified as code number VV-0373, not patented, as the female, or seed, parent with a proprietary selection of *Verbena* X *hybrida* identified as code number VV19-K0198, not patented, as the male, or pollen, parent. The new *Verbena* plant was discovered and selected by the Inventor as a single flowering plant within the progeny of the stated cross-pollination in a controlled greenhouse environment in Rheinberg, Germany in May 2021.

Asexual reproduction of the new *Verbena* plant by terminal vegetative cuttings in a controlled greenhouse environment in Rheinberg, Germany since May 2021 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doveremsunwhi 24'. These characteristics in combination distinguish 'Doveremsunwhi 24' as a new and distinct *Verbena* plant:

1. Relatively compact, mounding to semi-trailing plant habit.
2. Moderately vigorous growth habit and moderate growth rate.
3. Freely branching habit.

4. Early and freely flowering habit.
5. Large white-colored flowers.
6. Good container and garden performance.

Plants of the new *Verbena* differ primarily from plants of the female parent selection in the following characteristics:

1. Plants of the new *Verbena* are more mounding than and not as upright as plants of the female parent selection.
2. Plants of the new *Verbena* are more freely flowering than plants of the female parent selection.
3. Flowers of plants of the new *Verbena* are larger than flowers of plants of the female parent selection.

Plants of the new *Verbena* differ primarily from plants of the male parent selection in the following characteristics:

1. Plants of the new *Verbena* are more mounding than and not as upright as plants of the male parent selection.
2. Flowers of plants of the new *Verbena* are larger than flowers of plants of the male parent selection.

Plants of the new *Verbena* can be compared to plants of the *Verbena hybrida* 'Balendwite', disclosed in U.S. Plant Pat. No. 30,641. In side-by-side comparisons, plants of the new *Verbena* differ primarily from plants of 'Balendwite' in the following characteristics:

1. Plants of the new *Verbena* are more compact and more uniform than and not as vigorous and uneven as plants of 'Balendwite'.
2. Plants of the new *Verbena* are more freely branching than plants of 'Balendwite'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph on the first sheet (FIG. 1) is a side perspective view of a typical flowering plant of 'Doveremsunwhi 24' grown in a container.

Figure 2:
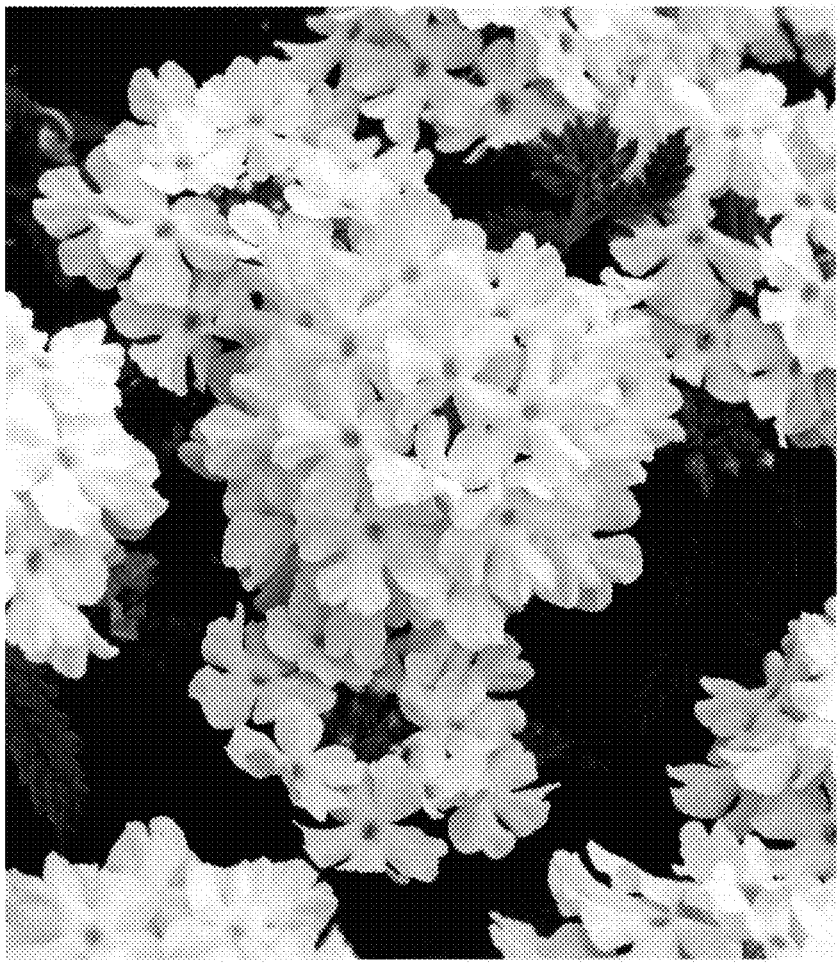

The photograph on the second sheet (FIG. 2) is a close-up view of a typical flowering plant of 'Doveremsunwhi 24'.

DETAILED BOTANICAL DESCRIPTION

The aforementioned photographs and following observations, measurements and values describe plants grown in 22-cm containers during the spring in a glass-covered greenhouse in Rheinberg, Germany and under cultural practices typical of commercial *Verbena* production. During the production of the plants, day and night temperatures averaged 18 C and light levels averaged 4,500 lux. Plants were pinched one time three weeks after planting and were 25 weeks old when the photographs and description were taken. In the description, color references are made to The Royal Horticultural Society Colour Chart, Fifth Edition, except where general terms of ordinary dictionary significance are used.

Botanical classification: *Verbena* X *hybrida* 'Doveremsunwhi 24'.

Parentage:

*Female, or seed, parent*.—Proprietary selection of *Verbena* X *hybrida* identified as code number VV-0373, not patented.

*Male, or pollen, parent*.—Proprietary selection of *Verbena* X *hybrida* identified as code number VV19-K0198, not patented.

Propagation:

*Type*.—Terminal vegetative cuttings.

*Time to initiate roots, summer*.—About five days at temperatures about 20 C.

*Time to initiate roots, winter*.—About seven days at temperatures about 20 C.

*Time to produce a rooted young plant, summer*.—About three weeks at temperatures about 20 C.

*Time to produce a rooted young plant, winter*.—About four weeks at temperatures about 20 C.

*Root description*.—Fine, fibrous; close to 158A in color, actual color of the roots is dependent on substrate composition, water quality, fertilizers, substrate temperature and age of roots.

*Rooting habit*.—Freely branching; medium density.

Plant description:

*Plant habit*.—Relatively compact, mounding to semi-trailing plant habit; freely branching habit with about eight primary lateral branches each with about six to seven secondary lateral branches; pinching enhances lateral branch development; dense and bushy plant habit; moderately vigorous growth habit and moderate growth rate.

*Plant height, soil level to top of foliar plane*.—About 17 cm.

*Plant height, soil level to top of floral plane*.—About 19 cm.

*Plant diameter*.—About 54 cm.

Lateral branch description:

*Length*.—About 29 cm.

*Diameter*.—About 4.8 mm.

*Internode length*.—About 5.7 cm.

*Strength*.—Strong.

*Texture and luster*.—Pubescent; semi-glossy.

*Color, developing*.—Close to 144B.

*Color, developed*.—Close to 137B.

Leaf description:

*Arrangement*.—Opposite, simple.

*Length*.—About 5 cm.

*Width*.—About 1.9 cm.

*Shape*.—Lanceolate.

*Apex*.—Acute.

*Base*.—Attenuate.

*Margin*.—Crenate; indentations medium in depth and divergent.

*Texture and luster, upper surface*.—Pubescent, coarse; semi-glossy.

*Texture and luster, lower surface*.—Pubescent, coarse; matte.

*Venation pattern*.—Pinnate.

*Color*.—Developing leaves, upper surface: Close to N137B. Developing leaves, lower surface: Close to 137C. Fully expanded leaves, upper surface: Close to N137C; venation, close to 146A. Fully expanded leaves, lower surface: Close to 137C; venation, close to 138A.

*Petioles*.—Length: About 3.9 mm. Diameter: About 1.8 mm. Strength: Moderately strong. Texture and luster, upper and lower surfaces: Smooth, glabrous; matte. Color, upper surface: Close to 145A. Color, lower surface: Close to 145B.

Flower description:

*Flower arrangement and habit*.—Salverform flowers arranged in hemispherical terminal umbels; umbels dense and mounding; numerous umbels per plant; flowers face upward or outwardly depending on position in the umbel; freely flowering habit with about 17 flowers per inflorescence and about 1,580 flowers and flower buds developing per plant during the flowering season.

*Fragrance*.—None detected.

*Natural flowering season*.—Plants flower continuously from the spring through the fall in Germany; plants begin flowering about eight weeks after planting.

*Flower longevity*.—Individual flowers last about one week on the plant; flowers persistent.

*Inflorescence height*.—About 3 cm.

*Inflorescence diameter*.—About 5.2 cm.

*Flower buds*.—Length: About 1.7 cm. Diameter: About 4 mm. Shape: Oval to tubular. Texture and luster: Rippled; matte. Color: Close to 1D.

*Flowers*.—Appearance: Salverform, five-parted fused corolla; lobes free. Diameter: About 2.4 cm. Depth: About 3.4 cm. Throat diameter: About 1.4 mm. Tube length: About 2.3 cm. Tube diameter: About 2 mm.

*Corolla*.—Arrangement: Single whorl of five fused petals. Petal lobe length: About 1.1 cm. Petal lobe width: About 1.1 cm. Petal lobe shape: Obovate, flat. Petal lobe apex: Emarginate. Petal margin: Entire. Petal texture and luster, upper and lower surfaces: Smooth, glabrous; matte. Throat texture and luster: Smooth, glabrous; matte. Tube texture and luster: Smooth, glabrous; matte. Color: Petal lobe, when opening and fully opened, upper surface: Close to NN155C; venation, close to NN155A; color becoming closer to NN155A with subsequent development. Petal lobe, when opening and fully opened, lower surface: Close to NN155C; venation, close to NN155C; color does not change with subsequent development. Throat: Close to 142A and 145B; venation, close to 145A. Tube: Close to 145C to 145D; venation, close to 145B.

*Calyx*.—Arrangement: Star-shaped calyx with five fused sepals. Length: About 1.5 cm. Diameter: About 2.1 mm. Sepal length: About 1.5 cm. Sepal width: About 1.5 mm. Sepal shape: Ligulate. Sepal apex: Acute. Sepal margin: Entire. Sepal texture and luster, upper surface: Pubescent, coarse; semi-glossy. Sepal texture and luster, lower surface: Pubescent, coarse; matte. Sepal color, upper and lower surfaces: Close to 137A and 145A.

*Peduncles*.—Length: About 2.1 cm. Diameter: About 1.5 mm. Strength: Strong. Aspect: Mostly upright. Texture and luster: Pubescent; semi-glossy. Color: Close to 144A to 144B.

*Pedicels*.—Length: About 0.6 mm. Diameter: About 0.6 mm. Strength: Strong. Aspect: Mostly upright. Texture and luster: Smooth, glabrous; semi-glossy. Color: Close to 144A.

*Reproductive organs*.—Stamens: Quantity and arrangement: About four per flower, adnate to corolla tube. Filament length: About 1 mm. Filament color: Close to 144D. Anther length: About 1 mm. Anther shape: Oval. Anther color: Close to 144C. Pollen amount: Moderate. Pollen color: Close to 8C. Pistils: Quantity: One per flower. Pistil length: About 2 cm. Style length: About 1.8 cm. Style color: Close to 144B, 144C and 144D. Stigma diameter: About 0.8 mm. Stigma shape: Bi-parted; fimbriate. Stigma color: Close to 144A. Ovary color: Close to 144A. Fruits: Quantity produced per plant: About 50 during the flowering season. Length: About 5 mm. Diameter: About 1 mm. Texture: Rough. Color: Close to 199C. Seeds: Quantity per flower: About four. Length: About 4.8 mm. Diameter: About 0.8 mm. Texture: Smooth, glabrous. Color: Close to 199B.

Garden performance: Plants of the new *Verbena* have been observed to have good garden performance, to tolerate temperatures ranging from 5 C to 40 C and to be hardy to USDA Hardiness Zone 11.

Pathogen & pest resistance: To date, plants of the new *Verbena* have not been observed to be resistant to pathogens and pests common to *Verbena* plants.

It is claimed:

1. A new and distinct *Verbena* plant named 'Doveremsunwhi 24' as herein illustrated and described.

* * * * *